United States Patent [19]

Tsai et al.

[11] Patent Number: 5,356,564
[45] Date of Patent: Oct. 18, 1994

[54] FERROELECTRIC LIQUID CRYSTAL MATERIALS AND LIQUID CRYSTAL COMPOSITIONS CONTAINING THE SAME

[75] Inventors: Wen-Liang Tsai, Hsinchu; Hwei-Long Kuo; Shu-Hui Yang, both of Taipei, all of Taiwan

[73] Assignee: Industrial Technology Research Institute, Hsinchu, Taiwan

[21] Appl. No.: 89,171

[22] Filed: Jul. 8, 1993

[51] Int. Cl.$^5$ .................. C09K 19/20; C09K 19/12; C07C 69/76; G02F 1/13

[52] U.S. Cl. .................. 252/299.64; 252/299.65; 252/299.66; 252/299.67; 560/76; 560/83; 359/103

[58] Field of Search .................. 252/299.01, 299.64, 252/299.65, 299.66, 299.67; 359/103; 560/76, 83, 102

[56] References Cited

PUBLICATIONS

Device Applications of Ferroelectric Liquid Crystals. Importance of Polarization Charge Interactions (SPIE vol. 1080 Liquid Crystal Chemistry, Physics, and Applications (1989)) pp. 110–139. (Author: Zhuang et al.).
CA:118(21):212689m.
CA:118(12):113701c.

*Primary Examiner*—Shean Wu
*Attorney, Agent, or Firm*—W. Wayne Liauh

[57] ABSTRACT

A liquid crystal composition containing an optically active or a ferroelectric liquid crystal compound represented by the following formula:

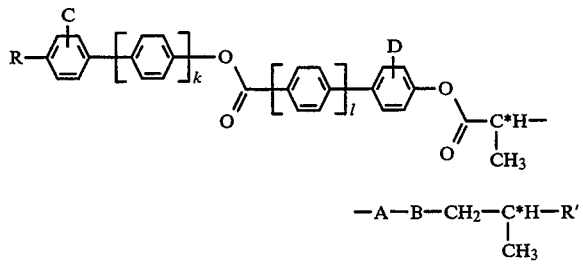

wherein: A is selected from the group consisting of oxygen and sulfur; B is selected from the group consisting of $-(CH_2)_m-$ and $-(CH_2)_n-O-$; R is an alkyl or alkoxyl group having 1 to 22 carbons; R' is an alkyl group having 2 to 8 carbons or an ether group having 2 to 8 carbons; m is an integer from 0 to 4; n is an integer from 2 to 5; k is an integer of 0 or 1; l is an integer of 0 or 1; C and D are selected form the group consisting of hydrogen atom and halogen atoms, and * represents a chiral center. The ferroelectric liquid crystals of the present invention exhibit optical and chemical stabilities, high-speed switching characteristic and high spontaneous polarization, and thus are excellent materials for use in liquid crystal devices and liquid crystal light switching elements.

19 Claims, No Drawings

FERROELECTRIC LIQUID CRYSTAL MATERIALS AND LIQUID CRYSTAL COMPOSITIONS CONTAINING THE SAME

FIELD OF THE INVENTION

This invention relates to a family of novel ferroelectric liquid crystal compounds and liquid crystal compositions containing the same. More particularly, this invention relates to a family of novel ferroelectric liquid crystal compounds, and liquid crystal compositions containing the same, which exhibit optical and chemical stability, high-speed switching characteristic, and high spontaneous polarization.

BACKGROUND OF THE INVENTION

Liquid crystal compounds have been widely used in display devices since the 1970's. Liquid crystal displays have many outstanding advantages in, for example, that they can be made to exhibit thin-thickness and light-weight, require low driving voltage and low power consumption, and are non-emissive. Because of these advantages, liquid crystal displays are widely considered as the mainstream display devices of the next generation.

Most of the conventional display devices are used in a TN-type display system, and nematic liquid crystal materials are most commonly used for this purpose. However, the TN display system has several limitations in the areas of response time and the width of the viewing angle. Therefore, in order to broaden the acceptance of liquid crystal display devices and utilize the advantages thereof as illustrated hereinabove, development of improved liquid crystal material as an alternative to the nematic phase type liquid crystal is essential.

Recently, ferroelectric liquid crystals have received significant attention as an alternative to the nematic type liquid crystals. In the past decade and half, over 500 patents have been issued in the areas related to ferroelectric liquid crystals. The existence of ferroelectric liquid crystals was first observed in 1974 which was subsequently published in 1975 by R. B. Meyer, L. Liebert, L. Strzelecki, and P. Keller (see J. Physique Letters, 1975, 36, L-69). They reported that strong ferroelectricity could be observed from liquid crystal belonging to a chiral smectic C phase (Sc* phase). They also synthesized a liquid crystal compound (S)-4-n-deecyloxybenzylideneamiao-2'-methylbutyl cinnamate (DOBAMBC) to prove their theory. In 1980, N. A. Clark and S. T. Lagerwall proposed a liquid crystal display system wherein an optical switching phenomenon of a ferroelectric liquid crystal was utilized. (See Appl. Phys. Lett., 1980, 36, 899; see, also, U.S. Pat. No. 4,367,924, entitled "Chiral Smectic C or H Liquid Crystal Electro-Optical Device"). The discovery of Clank and Lagerwall opened the door for ferroelectric liquid crystals to be used in practical applications.

Ferroelectric liquid crystals are known to have bistability. By definition, liquid crystals with bistability are those molecules which are horizontally oriented with respect to the electrode surface as stable state and are vertically oriented with respect to the electrode surface only when an electric field is effectively applied. Ferroelectric liquid crystals have bistable states of first and second stable states with respect to an electric field applied thereto. Accordingly, the bistable ferroelectric liquid crystals are oriented to the first and second optically stable states with respect to one and the other of the electric field vectors, respectively. Furthermore, ferroelectric liquid crystals have also shown to provide high-speed switching characteristic. This is because the high spontaneous polarization of the ferroelectric liquid crystals and an externally applied electric field directly interact with each other to induce transition of orientation states.

Ferroelectric liquid crystals also exhibit excellent characteristics of having high contrast and wide viewing angle, and thus are particularly suitable for use in large-sized displays using a simple matrix. These advantages, coupled with their bistability and high-speed switching characteristic, accord an excellent commercial potential for ferroelectric liquid crystals, especially in the area of flat-panel displays.

Ferroelectric liquid crystals belong to the family of tilted smectics; however, the most important ferroelectric liquid crystals belong to the chiral smectic C phase. In practical applications, a mixture of ferroelectric liquid crystals of various types, rather than a single type, are used. For those ferroelectric liquid crystals that do not exhibit the chiral smectic C phase, a chiral dopant can be added to a liquid crystal host. (See W. Kuczynski, H. Stegemeyer, Chem. Phys. Lett., 1980, 70, 123; S. M. Kelly, A. Villiger, Displays, 1990, 41.)

SUMMARY OF THE PRESENT INVENTION

The primary object of the present invention is to develop a family of novel ferroelectric liquid crystal compounds, and liquid crystal compositions comprising the same, which exhibit excellent optical and chemical stabilities, high spontaneous polarization, and high-speed switching characteristic, and thus can be used as an excellent base material in the manufacturing of liquid display devices. In the present invention, a liquid crystal compound refers to a liquid crystal molecule, and a liquid crystal composition refers to a liquid crystal mixture containing at least one liquid crystal molecule.

The family of ferroelectric liquid crystal compounds disclosed in the present invention are optically active esters having two chiral centers represented generally by the following formula:

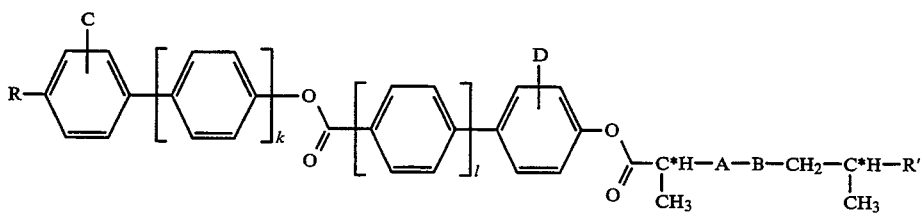

Formula (I)

wherein:

A: is selected from the group consisting of oxygen and sulfur;

B: is selected from the group consisting of —(CH$_2$)$_m$— and —(CH$_2$)$_n$—O—;

R: is an alkyl or alkoxyl group having 1 to 22 carbons;
R': is an alkyl group having 2 to 8 carbons or an ether group having 2 to 8 carbons;
m: is an integer from 0 to 4;
n: is an integer from 2 to 5;
k: is an integer of 0 or 1;
l: is an integer of 0 or 1;
C: is selected from the group consisting of hydrogen atom, or a halogen atom;
D: is selected form the group consisting of hydrogen atom, or a halogen atom; and
*: represents a chiral center.

In formula (I), C can be the same as, or different from, D.

In preferred embodiments, B is $-(CH_2)_m-$, m is 0, R is a linear alkoxyl group having 3 to 12 carbons, R' is an ethyl group, C and D are either hydrogen or fluoride atom, and either k or l is one.

The liquid crystal composition disclosed in the present invention can comprise one or more of the ferroelectric liquid crystal compounds represented by formula (I). Optionally, the liquid crystal composition disclosed in the present invention can be a mixture which comprises one or more of the ferroelectric compounds represented by formula (I), and a smectic C phase (Sc* phase) liquid crystal, or a chiral Sc* phase liquid crystal. The present invention also discloses a liquid crystal device containing one or more of the compounds represented by formula (I), or a mixture containing the same, confined between two electrode plates. The compound represented by formula (I), or a mixture containing the same, can also be used in a light switching element. The dual chiral centers shown in formula (I) enable the compounds of the present invention to exhibit improved characteristics as ferroelectric liquid crystals.

DETAILED DESCRIPTION OF PREFERRED EMBODIMENT

The present invention will now be described more specifically with reference to the following examples. It is to be noted that the following descriptions of examples including preferred embodiments of this invention are presented herein for purpose of illustration and description; it is not intended to be exhaustive or to limit the invention to the precise form disclosed.

EXAMPLE 1

In Example 1, the ferroelectric liquid crystal compound as represented by formula (I) has R=octoxyl group, R'=ethyl group, A=oxygen atom, B=$-(CH_2)_m-$, m=0, k=0, l=1, and C and D are both hydrogen atoms.

The first step of the reaction in Example 1 involved preparing reaction solution A. In the first step, 3.56 g (10 mmol) of compound 1, as represented by the following formula:

(Compound 1)

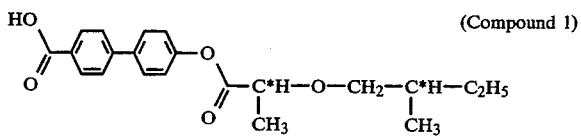

was dissolved in 10 ml benzene. Then 10 mmol of oxalyl chloride (COCl)$_2$ was slowly added to the solution, in a 10-minute span. Dimethylformamide (DMF) was also added as a catalyst. The solution was stirred at room temperature for three hours and was placed in a 30 mm Hg vacuum to remove excess oxalyl chloride. The reaction system was returned to normal pressure by introducing dry nitrogen. Thereafter, 10 ml dichloromethane was added to the solution to form reaction solution A.

Compound 1 was prepared by the following procedure:

Step A: 4.3 g (20 m-mol) of 4'-hydroxy-4-biphenyl-carboxylic acid (from Aldrich, U.S.A.) was dissolved into 20 ml of dimethyl formamide (DMF) to form "solution A". Then 3.5 g (20 m-mol) of benzylbromide (also from Aldrich, U.S.A.) was dissolved into 10 ml DMF to form "solution B". Solution A was gradually injected, using a syringe, into a 100-ml round-bottomed flask containing 1.6 g (40 m-mol) of 60% NaH and 10 ml DMF. The sodium hydride had been washed with hexane to remove mineral oil. The mixture was stirred for 10 minutes. Solution B was then gradually injected into the mixture solution, also using a syringe. The mixture was stirred again for 14 hours, and the solvent was removed by evaporation. The residue was dissolved in ethyl ether and filtered to obtain filtrate, which was rinsed with water to collect the organic layer. After the solvent was removed, the product was subject to column chromatography (hexane/ethyl acetate/chloroform 3/1/1), and the middle portion was collected. The product was represented by the following formula:

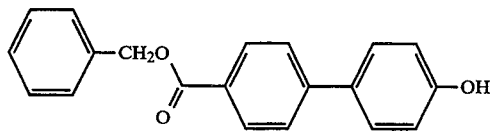

The yield was 75%.

Step B: 3.35 g (11 m-mol) of the compound obtained from Step A, 1.6 g (10 m-mol) of an optically active organic acid represented by the following formula:

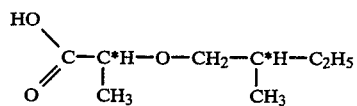

0.12 g (1 m-mol) of 4-(N,N-dimethylamino) pyridine (DMAP), 2.3 g (11 m-mol) of dicyclohexylcarbodiimide (DCC) and 25 ml of dry dichloromethane were added to a 50-ml round bottomed flask and purged with nitrogen. The mixture was stirred at room temperature for 10-14 hours. After the precipitate was removed, the filtrate was added with equal amount of dichloromethane, and washed with dilute hydrochloric acid, then deionized water. The final product, which was purified by liquid column chromatography (hexane/ethyl acetate 4/1), was presented by the following formula:

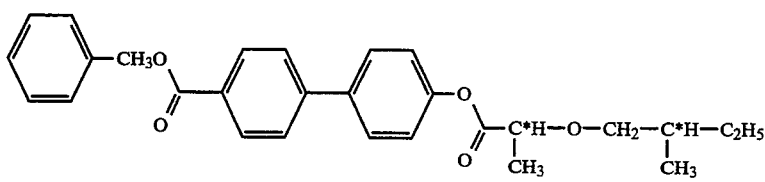

Step C: 5 m-mol of the product from Step B, 80 ml of ethanol, 40 ml of cyclohexene, and 0.4–0.5 g of 10% of Pd/C were added to a 100-ml round-bottomed flask, and stirred at room temperature over night. The Pd/C was removed via filtration with Celite. Compound 1 was then obtained after the solvent was removed by vaporization. The yield was about 95%. While this purity was generally good enough to conduct next step reactions, further purification may be achieved using ethanol or hexane crystallization.

Reaction solution B was prepared by dissolving compound 2, which is represented by the following formula:

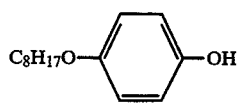

(Compound 2)

into a solution mixture containing 1 ml pyridine and 10 ml dichloromethane. This formed reaction solution B.

Solution B was slowly added into solution A, in a time span of five minutes. The resultant mixture solution was stirred for twelve hours, and then placed in a vacuum to remove solvents. After recrystalization using hexane, 3.86 g of solid product, which had the following formula:

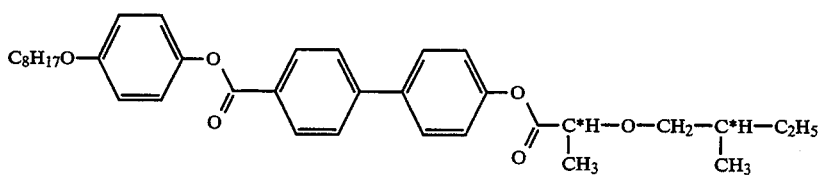

(Compound 3)

was obtained. The reaction yield was calculated to be 70%. The reaction product, designated as Compound 3, had an optical rotation $[\alpha_D^{25} = -32°$ (c=1.0, CHCl$_3$). The NMR results of Compound 3 are summarized below:

$^1$H NMR (CDCl$_3$)δ8.27(d, 2H, J8.6), 7.73~7.65 (overlapped peaks, 4H), 7.24 (d, 2H, J8.8), 7.15 (d, 2H, J9.1), 6.95 (d, 2H, J9.1), 4.21 (q, 1H, J6.8), 3.96 (t, 2H, J6.5), 3.59 (AB d, 1H, J8.8 6.2), 3.29 (AB d, 1H, J8.8 6.7), 1.9~1.1 (overlapped peaks, 18H), 1.05~0.85 (overlapped peaks, 9H). $^{13}$C NMR (CDCl$_3$)δ172.04, 165.34, 156.92, 150.66, 145.18, 144.21, 137.74, 130.71 (2C), 128.53, 128.44 (2C), 127.14 (2C), 122.38 (2C), 121.94 (2C), 115.1 (2C), 75.91, 75.23, 68.42, 35.12, 31.83, 29.37, 29.27 (2C), 26.15, 26.06, 22.68, 18.67, 16.54, 14.12, 11.28.

EXAMPLE 2

In Example 2, the ferroelectric liquid crystal compound as represented by formula (I) has R=octoxyl group, R'=ethyl group, A=oxygen atom, B=—(CH$_2$)$_m$—, m=0, k=1, l=0, and both C and D are hydrogen atoms.

The first step of the reaction in Example 2 involved preparing reaction solution C. 10 mmol of Compound 4, which was represented by the following formula:

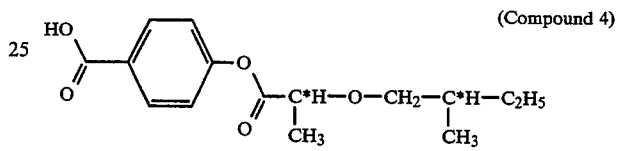

(Compound 4)

was dissolved in 10 ml benzene. Then 10 mmol of oxalyl chloride (COCl)$_2$ was slowly added to the solution, in a 10-minute span. Dimethylformamide (DMF) was also added as a catalyst. The solution was stirred at room temperature for three hours and was placed in a 30 mm Hg vacuum to remove excess oxalyl chloride. The reaction system was returned to normal pressure by introducing dry nitrogen. Thereafter, 10 ml dichloromethane was added to the solution to form reaction solution C.

Reaction solution D was prepared by dissolving Compound 5, which was represented by the following formula:

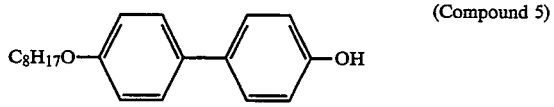

(Compound 5)

into a solution mixture containing 1 ml pyridine and 10 ml dichloromethane. This formed reaction solution D.

Solution D was slowly added into solution C, in a time span of five minutes. The mixture solution was stirred for twelve hours, and then placed in a vacuum to remove solvents. After recrystalization using hexane, a solid product, which had the following formula:

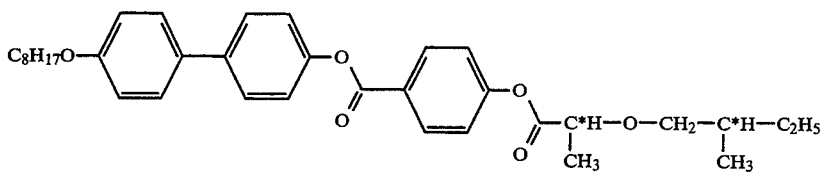

(Compound 6)

was obtained. The reaction yield was calculated to be 72%. The product, designated as Compound 6, had an optical rotation $[\alpha]_D^{25} -33°$ (c=1.15, CHCl$_3$). The NMR results Compound 6 are summarized below:

$^1$H NMR (CDCl$_3$)δ8.28 (d,2H, J8.8), 7.70~7.45 (overlapped peaks, 4H), 7.35~7.20 (overlapped peaks, 4H), 6.98 (d, 2H, J8.8), 4.21 (q, 1H, J6.8), 4.00 (t, 2H, J6.5), 3.59 (AB d, 1H, J8.8 6.1), 3.28 (AB d, 1H, J8.8 6.6), 1.9~1.1(overlapped peaks, 18H), 1.05~0.85 (overlapped peaks, 9H). $^{13}$C NMR (CDCl$_3$)δ171.50, 164.42, 158.81, 154.66, 149.72, 138.85, 132.65, 131.87 (2C), 128.10 (2C), 127.44 (2C), 127.24, 121.84 (2C), 121.67 (2C), 114.81 (2C), 75.97, 75.21, 68.10, 35.13, 31.83, 29.27 (2C), 26.13, 26.07, 22.68, 18.62, 16.51, 14.13, 11.27.

EXAMPLE 3

In Example 3, the chiral compound as represented by formula (I) has R=octoxyl group, R'=ethyl group, A=oxygen atom, B=—(CH$_2$)$_m$—, m=0, k=0, l=0, and both C and D are hydrogen atoms.

The first step of the reaction in Example 3 involved preparing reaction solution E. Compound 4, whose formula was disclosed in Example 2, was dissolved in 10 ml benzene. Then 10 mmol of oxalyl chloride (COCl)$_2$ was slowly added to the solution, in a 10-minute span. Dimethylformamide (DMF) was also added as a catalyst. The solution was stirred at room temperature for three hours and was placed in a 30 mm Hg vacuum to remove excess oxalyl chloride. The reaction system was returned to normal pressure by introducing dry nitrogen. Thereafter, 10 ml dichloromethane was added to the solution to form reaction solution E.

Reaction solution F was prepared by dissolving compound 2, whose formula was disclosed in Example 1, into a solution mixture containing 1 ml pyridine and 10 ml dichloromethane. This formed reaction solution F.

Solution F was slowly added into solution E, in a time span of five minutes. The mixture solution was stirred for twelve hours, and then placed in a vacuum to remove solvents. After recrystalization using hexane, a solid product, which had the following formula:

$^1$H NMR (CDCl$_3$)δ8.23 (d, 2H, J8.9), 7.24 (d, 2H, J8.9), 7.09 (d, 2H, J8.9), 6.91 (d, 2H, J9.1), 4.18 (q, 1H, J6.9), 3.95 (t, 2H, J6.5), 3.56 (AB d, 1H, J8.7 6.2), 3.28 (AB d, 1H, J8.7 6.6), 1.9~1.1 (overlapped peaks, 18H), 1.00~0.85 (overlapped peaks, 9H). $^{13}$C NMR (CDCl$_3$)δ171.48, 164.67, 156.94, 154.54, 144.08, 131.76 (2C), 127.33, 122,30 (2C), 121.58 (2C), 115.09 (2C), 75.94, 75.18, 68.39, 31.76, 29.25, 29.05 (2C), 26.10, 25.98, 22.59, 18.58, 16.48, 14.08, 11.24.

EXAMPLES 4-18

Fifteen different compounds were prepared according to the procedures described in Examples 1-3. The type of liquid crystal phase, phase transition temperature, and optical rotation of the eighteen compounds prepared from Examples 1-18, which include six optically active compounds and twelve ferroelectric liquid crystals, are summarized in Table 1.

EXAMPLES 19-30

Twelve ferroelectric liquid crystals prepared from previous examples and listed in Table 1 were tested using the triangular wave method and the electric reverse method, both of which have been disclosed in the prior art (see, K. Miyasato et al., Jpn. J. Appl. Phys. 22, L661 and K. Sharp et al., Mol. Cryst. Liq. Cryst., 114, 283, respectively). Each of these ferroelectric liquid crystals was sandwiched between two glass electrode plates, and the gap between the two glass plates was 2 microns. The test results are summarized in Table 1.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present

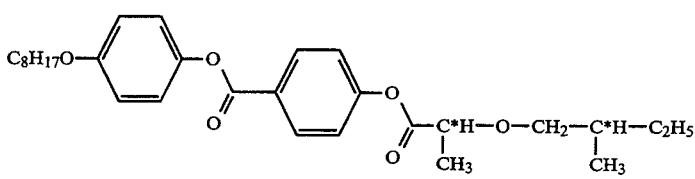

(Compound 7)

was obtained. The reaction yield was calculated to be 80%. The product, designated as compound 7, had an optical rotation $[\alpha_D^{25} = -29°$ (c=1.15, CHCl$_3$). The NMR results of compound 7 are summarized below:

invention as determined by the appended claims when interpreted in accordance with the breadth to which they are fairly, legally, and equitably entitled.

TABLE 1

| Compound Identification | | | | Liquid Crystal Phase and Phase Transition Temperature (°C.) | | | | | | | | Physical Characteristics | | |
|---|---|---|---|---|---|---|---|---|---|---|---|---|---|---|
| Compound | R | k | l | C | | Sc* | | N* | | I | | Ps (nC/cm²) | τ (μs) | [α]$_D^{25}$ (CHCl₃) |
| 3a | C₆H₁₃O | 1 | 0 | * | 121 | * | 137 | * | 146 | * | | 141 | — | −33 |
| 3b | C₇H₁₅O | 1 | 0 | * | 120 | * | 130 | * | 134 | * | | 150 | 52 | −33 |
| 3c | C₈H₁₇O | 1 | 0 | * | 115 | * | 135 | * | 139 | * | | 132 | 80 | −32 |
| 3d | C₉H₁₉O | 1 | 0 | * | 104 | * | 131 | * | 133 | * | | 155 | — | −30 |
| 3e | C₁₀H₂₁O | 1 | 0 | * | 103 | * | 134 | * | — | * | | 123 | 85 | −30 |
| 3f | C₁₂H₂₅O | 1 | 0 | * | 106 | * | 129 | * | — | * | | 95 | 100 | −29 |
| 6a | C₆H₁₃O | 0 | 1 | * | 88 | * | 127 | * | 135 | * | | 48 | 23 | −32 |
| 6b | C₇H₁₅O | 0 | 1 | * | 85 | * | 124 | * | 128 | * | | — | 30 | −34 |
| 6c | C₈H₁₇O | 0 | 1 | * | 87 | * | 120 | * | 125 | * | | 44 | 38 | −33 |
| 6d | C₉H₁₉O | 0 | 1 | * | 86 | * | 125 | * | 127 | * | | — | 28 | −34 |
| 6e | C₁₀H₂₁O | 0 | 1 | * | 91 | * | 118 | * | 120 | * | | 45 | 62 | −34 |
| 6f | C₁₂H₂₅O | 0 | 1 | * | 89 | * | 121 | * | 123 | * | | 46 | 44 | −33 |
| 7a | C₆H₁₃O | 0 | 0 | * | 35 | — | — | — | — | * | | — | — | −32 |
| 7b | C₇H₁₅O | 0 | 0 | * | 40 | — | — | — | — | * | | — | — | −31 |
| 7c | C₈H₁₇O | 0 | 0 | * | 45 | — | — | — | — | * | | — | — | −29 |
| 7d | C₉H₁₉O | 0 | 0 | * | 50 | — | — | — | — | * | | — | — | −31 |
| 7e | C₁₀H₂₁O | 0 | 0 | * | 52 | — | — | — | — | * | | — | — | −32 |
| 7f | C₁₂H₂₅O | 0 | 0 | * | 60 | — | — | — | — | * | | — | — | −30 |

Note:
C represents solid state; Sc* represents chiral smectic C phase; N* represents chiral nematic phase; I represents liquid phase; Ps represents "spontaneous polarization" value; τ represents response time. Both Ps and τ were measured at a temperature which was 10° C. below the phase transition temperature between Sc* and N* phases.

What is claimed is:

1. An optically active liquid crystal compound represented by the following formula:

(Formula I)

$$R-\underset{C}{\bigcirc}-[\bigcirc]_k-O-\underset{O}{\overset{\parallel}{C}}-[\bigcirc]_l-\underset{D}{\bigcirc}-O-\underset{O}{\overset{\parallel}{C}}-\underset{CH_3}{\overset{|}{C^*H}}-A-B-CH_2-\underset{CH_3}{\overset{|}{C^*H}}-R'$$

wherein:
A: is selected from the group consisting of oxygen and sulfur;
B: is selected from the group consisting of —(CH₂)$_m$— and —(CH₂)$_n$—O—;
R: is an alkyl or alkoxyl group having 1 to 22 carbons;
R': is an alkyl group having 2 to 8 carbons or an ether group having 2 to 8 carbons;
m: is an integer from 0 to 4;
n: is an integer from 2 to 5;
k: is an integer of 0 or 1;
l: is an integer of 0 or 1;
C: is selected from the group consisting of hydrogen atom and halogen atoms;
D: is selected from the group consisting of hydrogen atom and halogen atoms; and
*: represents a chiral center.

2. The optically active liquid crystal compound of claim 1 wherein R is a linear alkoxyl group having 3 to 12 carbons.

3. The optically active liquid crystal compound of claim 1 wherein R is a linear alkyl group having 3 to 12 carbons.

4. The optically active liquid crystal compound of claim 1 wherein A is an oxygen atom.

5. The optically active liquid crystal compound of claim 1 wherein B is —(CH₂)$_m$— and m is an integer from 0 to 4.

6. The optically active liquid crystal compound of claim 5 wherein m is zero.

7. The optically active liquid crystal compound of claim 1 wherein C and D are either hydrogen or fluoride atom.

8. The optically active liquid crystal compound of claim 1 wherein R' is an ethyl group.

9. The optically active liquid crystal compound of claim 1 which is represented by the following formula:

(Formula II)

$$RO-\bigcirc-O-\underset{O}{\overset{\parallel}{C}}-\bigcirc-O-\underset{O}{\overset{\parallel}{C}}-\underset{CH_3}{\overset{|}{C^*H}}-O-CH_2-\underset{CH_3}{\overset{|}{C^*H}}-C_2H_5$$

wherein R is a linear alkyl group having 1 to 22 carbons and * represents a chiral center.

10. A ferroelectric liquid crystal compound represented by the one of the following formulas:

(Formula III)

$$RO-\bigcirc-\bigcirc-O-\underset{O}{\overset{\parallel}{C}}-\bigcirc-O-\underset{O}{\overset{\parallel}{C}}-\underset{CH_3}{\overset{|}{C^*H}}-O-CH_2-\underset{CH_3}{\overset{|}{C^*H}}-C_2H_5$$

or

-continued

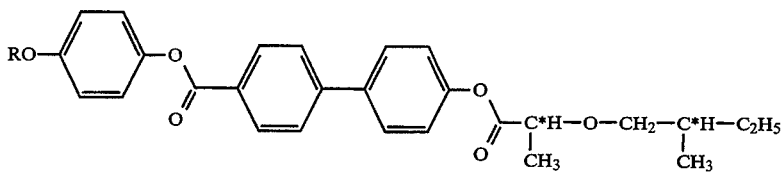
(Formula IV)

wherein R is a linear alkyl group having 1 to 22 carbons and * represents a chiral center.

11. A active liquid crystal composition comprising a optically active liquid crystal compound represented by the following formula:

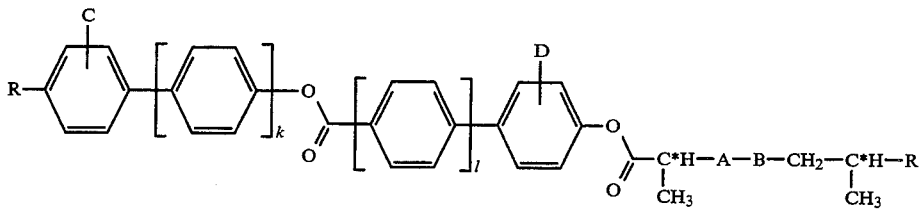
(Formula I)

wherein:
A: is selected from the group consisting of oxygen and sulfur;
B: is selected from the group consisting of —(CH$_2$)$_m$— and —(CH$_2$)$_n$—O—;
R: is an alkyl or alkoxyl group having 1 to 22 carbons;
R': is an alkyl group having 2 to 8 carbons or an ether group having 2 to 8 carbons;
m: is an integer from 0 to 4;
n: is an integer from 2 to 5;
k: is an integer of 0 or 1;
l: is an integer of 0 or 1;
C: is selected from the group consisting of hydrogen atom, a halogen atom;
D: is selected from the group consisting of hydrogen atom, a halogen atom; and
*: represents a chiral center.

12. The liquid crystal composition of claim 11 which further comprises a smectic C phase liquid crystal or a chiral smectic C phase liquid crystal, or a mixture thereof.

13. A liquid crystal device comprising the liquid crystal composition according to claim 11 which is paced between a pair of plates.

14. A liquid crystal light switching device comprising the liquid crystal composition according to claim 11.

15. An optically active compound represented by the following formula:

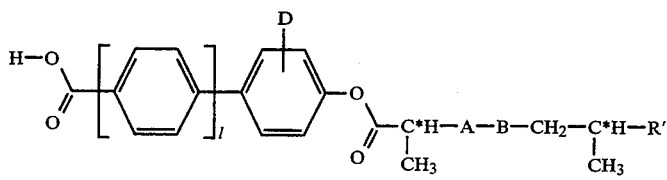
(Formula V)

wherein:

A: is selected from the group consisting of oxygen and sulfur;
B: is selected from the group consisting of —(CH$_2$)$_m$— and —(CH$_2$)$_n$—O—;
R': is an alkyl group having 2 to 8 carbons or an ether group having 2 to 8 carbons;
m: is an integer from 0 to 4;
n: is an integer from 2 to 5;
l: is an integer of 0 or 1;
D: is selected from the group consisting of hydrogen atom and halogen atoms; and
*: represents a chiral center.

16. The optically active compound of claim 15 which is represented by the following formula:

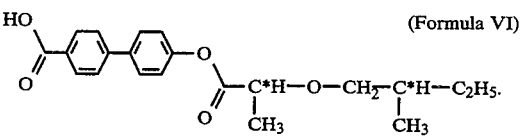
(Formula VI)

17. The optically active compound of claim 15 which is represented by the following formula:

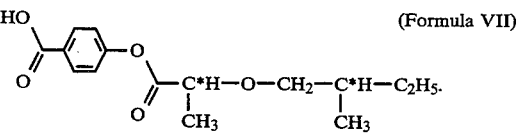
(Formula VII)

18. The optically active liquid crystal compound according to claim 1 wherein when k=0 then l≠0.

19. The optically active liquid crystal compound according to claim 11 wherein when k=0 then l≠0.

* * * * *